(12) United States Patent
Tomlinson et al.

(10) Patent No.: US 8,692,031 B2
(45) Date of Patent: Apr. 8, 2014

(54) METHOD FOR PREPARING POLYAMINE COMPOUNDS

(75) Inventors: Ian Anthony Tomlinson, Midland, MI (US); Glenn Nelson Robinson, Naperville, IL (US); Asghar Akber Peera, Cary, IL (US)

(73) Assignees: Dow Global Technologies LLC, Midland, MI (US); ANGUS Chemical Company, Buffalo Grove, IL (US)

( * ) Notice: Subject to any disclaimer, the term of this patent is extended or adjusted under 35 U.S.C. 154(b) by 149 days.

(21) Appl. No.: 13/500,449

(22) PCT Filed: Oct. 8, 2010

(86) PCT No.: PCT/US2010/052004
§ 371 (c)(1),
(2), (4) Date: Apr. 5, 2012

(87) PCT Pub. No.: WO2011/044478
PCT Pub. Date: Apr. 14, 2011

(65) Prior Publication Data
US 2012/0202934 A1     Aug. 9, 2012

Related U.S. Application Data

(60) Provisional application No. 61/278,530, filed on Oct. 8, 2009.

(51) Int. Cl.
*C07C 201/12* (2006.01)
*C07C 205/15* (2006.01)
*C07C 213/02* (2006.01)
*C07C 215/18* (2006.01)

(52) U.S. Cl.
USPC ............................ 568/712; 568/944; 564/495

(58) Field of Classification Search
None
See application file for complete search history.

(56) References Cited

FOREIGN PATENT DOCUMENTS

DE     10318143     9/2004

OTHER PUBLICATIONS

Benson, et al., "Synthesis and Reactivity of Captodative Diradical Oligomers Incorporating the 3, 5, -Trimethyl-2-oxomorpholin-3-yl (TM-3) Unit", J. Org. Chem., vol. 53, pp. 3036-3045 (1988).
Gaudiano, et al., "Synthesis of a Capto-Dative Diradical and Its Reversible Oligomerization to Macrocycles of Coronand Structure", J. Am. Chem. Soc., vol. 106, pp. 7628-7629 (1984).

*Primary Examiner* — Brian J Davis
(74) *Attorney, Agent, or Firm* — Kenneth Crimaldi

(57) ABSTRACT

A method for preparing a compound having formula (II)

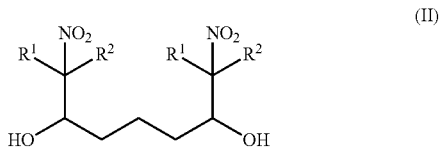

wherein $R^1$ and $R^2$ independently are methyl or ethyl, or $R^1$ and $R^2$ combine to form a $C_5$ or $C_6$ cycloalkyl or cycloalkenyl group. The method includes a step of combining $R^1R^2CHNO_2$, glutaraldehyde and an amine. The compound is useful in coating compositions and other applications for pH adjustment.

9 Claims, No Drawings

METHOD FOR PREPARING POLYAMINE COMPOUNDS

BACKGROUND

This invention relates generally to a method for preparing a polyamine compound, e.g., a bis-AMP compound useful in coating compositions and other applications for pH adjustment.

AMP (2-amino-2-methylpropanol) is used for pH adjustment of coating compositions and other formulations requiring pH adjustment. Compounds useful for this purpose, but having lower volatility, as measured by standard VOC (volatile organic compound) tests would be desirable. Benson et al., *J. Org. Chem.*, 1988, 53 3036-3045, disclose a compound having the formula (I)

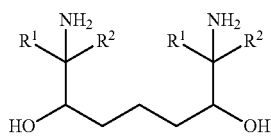

but this reference merely uses this compound as an intermediate for production of biologically active substances, and does not disclose or suggest that this compound could be useful for pH adjustment of industrial formulations. Moreover, the yield of the nitro compound precursor to the compound of formula (I) is very low, making this compound an unattractive option for industrial uses.

The problem addressed by this invention is to find low-VOC polyamine compounds useful in coating compositions and other applications for pH adjustment, and to provide an improved method for producing such compounds and their precursors.

STATEMENT OF INVENTION

The present invention is directed to a method for preparing a compound having formula (II)

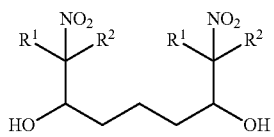

wherein $R^1$ and $R^2$ independently are methyl or ethyl, or $R^1$ and $R^2$ combine to form a $C_5$ or $C_6$ cycloalkyl or cycloalkenyl group. The method comprises combining $R^1R^2CHNO_2$, glutaraldehyde and a $C_6$-$C_{12}$ trialkylamine. The compound of formula (II) can be contacted with a reducing agent capable of reducing aliphatic nitro groups to produce a compound of formula (I)

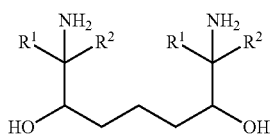

The present invention is further directed to a method for adjusting pH in an aqueous coating composition; said method comprising adding to a coating composition having a pH below 7 a sufficient amount of a compound of formula (I) to produce a final pH from 7.5 to 9.5; wherein $R^1$ and $R^2$ independently are methyl or ethyl, or $R^1$ and $R^2$ combine to form a $C_5$ or $C_6$ cycloalkyl or cycloalkenyl group.

DETAILED DESCRIPTION

All percentages are weight percentages ("wt %"), unless otherwise indicated. Concentrations in parts per million ("ppm") are calculated on a weight/volume basis. An "aqueous" composition is one comprising at least 30 wt % water, alternatively at least 35 wt % water, alternatively at least 38 wt % water. Preferably, aqueous compositions comprise no more than 5 wt % organic solvent. An "alkyl" group is a hydrocarbyl group having from one to twenty carbon atoms, unless otherwise specified, in a linear or branched arrangement. An alkenyl group is an alkyl group having one or more double bonds, preferably one double bond. A "cycloalkyl" or "cycloalkenyl" group is an alkyl or alkenyl group containing at least one ring.

In some embodiments of the invention, $R^1$ is methyl, $R^2$ is methyl or ethyl, or $R^1$ and $R^2$ combine to form a $C_6$ cycloalkyl group; alternatively $R^1$ is methyl, $R^2$ is methyl or ethyl, or $R^1$ and $R^2$ combine to form a cyclohexyl group; alternatively $R^1$ is methyl and $R^2$ is methyl or ethyl; alternatively $R^1$ and $R^2$ are methyl.

The improved method of this invention for producing compound (II) comprises combining $R^1R^2CHNO_2$, glutaraldehyde and a $C_6$-$C_{12}$ trialkylamine. Any alkyl group in the trialkylamine may contain a hydroxy group. In some embodiments of the invention, the $C_6$-$C_{12}$ trialkylamine is selected from the group consisting of triethylamine, dimethylethanolamine, di-isopropylethylamine, dimethyl isopropylamine, dimethylcyclohexylamine, N,N-dimethyl-2-amino-2-methylpropanol (DMAMP), and combinations thereof; alternatively triethylamine, dimethylethanolamine, dimethylcyclohexylamine, DMAMP and combinations thereof. Alternatives for $R^1$ and $R^2$ are as stated above. Particularly preferred nitro compounds, $R^1R^2CHNO_2$, are 2-nitropropane, 2-nitrobutane and nitrocyclohexane.

In some embodiments of the invention, reduction of compound (II) to compound (I) may be accomplished using any reagent capable of reducing aliphatic nitro groups. Examples of such reducing agents include hydrogen gas in combination with a catalyst, for example, Raney nickel or a platinum- or palladium-based catalyst (Pt or Pd in elemental form or as oxides, with or without supports, e.g., carbon); and other reducing agents including metal/acid combinations, e.g., iron/acetic acid; and aluminum hydrides, e.g., VITRIDE. Preferred reducing agents include hydrogen gas in combination with any of the following catalysts: Raney nickel, platinum or palladium. Conditions for hydrogenation of nitro groups are well known, e.g., a temperature range of about 20-80° C. at a pressure of about 100-1000 psi (690 kPa-6900 kPa), and these can be adjusted easily by one skilled in the art.

When the compound of formula (I) is used to adjust pH in an aqueous coating composition or other aqueous composition having an initial pH less than 7, the amount of compound (I) added clearly can vary depending on the initial pH, desired final pH, and other components present in the composition. However, one skilled in the art can easily determine the necessary amount of compound (I). In acrylic latex coating compositions, typically the amount of compound (I) would be in the range from 10 wt % to 125 wt % of total weight of carboxylic acid groups in the coating composition, alternatively from 25 wt % to 100 wt %. In some embodiments of the invention, the initial pH of the aqueous composition is from 2-7, alternatively from 2.5-6. The target pH value preferably is from 7.8 to 9.3, alternatively from 8 to 9.2. In some embodiments of the invention, the aqueous coating composition is an acrylic latex comprising copolymers of acrylic or methacrylic acid with $C_1$-$C_8$ alkyl acrylates or methacrylates. In some embodiments of the invention, the acrylic latex comprises 40-65 wt % polymer solids, alternatively 45-62 wt %, alternatively 45-55 wt %.

EXAMPLES

Preparation of 2,8-dimethyl-2,8-dinitrononane-3,7-diol (1)

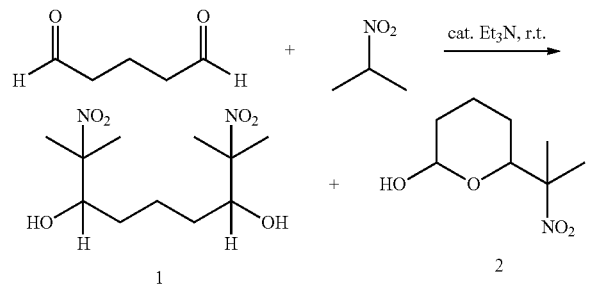

A 3 neck round bottom flask equipped with a stir bar, dropping funnel and nitrogen outlet was charged with 2-nitropropane (50 g, 0.57 mol) and 50 mL of methanol. The mixture was stirred for 10 minutes and triethylamine (2.8 g, 5 mol %) was added. The pale yellow solution was stirred for additional 15 minutes. To the above mixture 50% glutaraldehyde solution (56.7 g, 0.28 mol) was added drop wise over a period of 90 minutes via a dropping funnel. After completion of the addition, the solution was allowed to stir at room temperature for 48 h. The solution was poured in a separatory funnel containing 150 mL of ice water. The two phases were separated and the aqueous layer was extracted (2×50 mL) with diethyl ether. The combined organic phase were washed with (2×50 mL) of water and dried over anhydrous magnesium sulfate and filtered. The solvent was removed by rotary evaporator and the viscous residue was diluted in with 20 mL of ethyl acetate and cooled in an ice bath. A white precipitate gradually formed at the bottom of the flask and was separated by suction filtration. The white powder was air dried followed by drying in vacuo at 60° C. for 1 h. The yield after drying in vacuo was 23.3 g (30%) of the desired compound. $^1$H NMR (DMSO-$d_6$): ∂1.43 (broad s, 18H), ∂3.80 (m, 2H) and ∂5.31 (d, 2H, J=7.2 Hz). $^{13}$C NMR (DMSO-$d_6$): ∂19.4, 22.5, 22.8, 30.5, 74.9 and 92.1 ppm. HPLC retention time was 3.99 minutes and the melting point recorded for the solid was 136-138° C. The molecule was too bulky to show up on GC/MS at the set conditions. The yield was significantly higher than that obtained in Benson et al., *J. Org. Chem.*, 1988, 53 3036-3045 (23%). In that reference, potassium carbonate was used as the base.

The balance of the product mixture was identified as the cyclic product 6-(2-nitropropan-2-yl)-tetrahydro-2H-pyran-2-ol (2). Due to the presence of two chiral centers, several diastereomeric mixtures of the products were formed. The product was identified by GC having retention time of 16.9 min. The molecular ion peak m/z 142 (The molecular weight of the pyranol minus the $NO_2$ fragment) was observed in GC/MS.

Preparation of 2,8-diamino-2,8-dimethylnonane-3,7-diol (3)

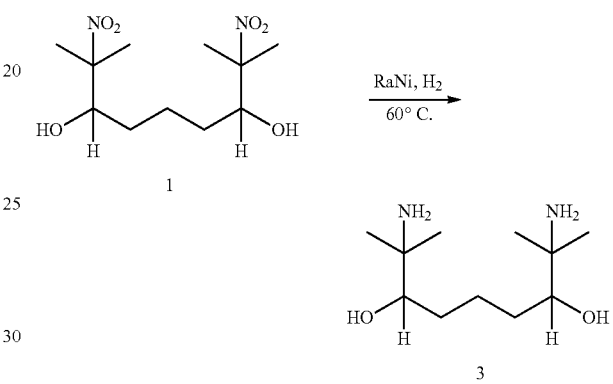

A 2-liter stirred PARR autoclave is charged with RaNi 3111 (72.1 g) and 300 mL of methanol. The autoclave is sealed and purged via 3 cycles of pressurizing 50 psi $N_2$ followed by venting to 5 psi. This is also repeated using $H_2$ gas. After purging, the pressure of the autoclave is increased to 450 psi of $H_2$. The sealed reactor is then stirred at 600 rpm and the heater switched on at this time. The pressure is increased to 600 psi once the temperature reaches 60° C. At this point the 2,8-dimethyl-2,8-dinitrononane-3,7-diol dissolved in 600 mL of Methanol is added into the autoclave containing RaNi at 5 mL/minute via a pump. After complete addition, the pump is switched off and the content of the autoclave stirred at 60° C. for 1 h, followed by stirring at 45° C. for additional 0.5 h. The content in the autoclave is cooled down to room temperature, the residual hydrogen is vented and the reactor opened. The product is filtered from the RaNi through suction filtration and excess methanol removed by rotary evaporator. This process resulted into 98 g (83%) of viscous oil. GC/MS analysis showed the desired product was present in 75%, with [MH]$^+$ m/z 219.

The rest of the product was 6-(2-aminopropan-2-yl)-tetrahydro-2H-pyran-2-ol and 6-methyl-6-nitroheptane-1,5-diol. These are the reduced form and opened ring form of the cyclic nitro alcohol formed as side product during the Henry reaction. The presence of both these products was confirmed by GC/MS.

VOC Test Procedure for Raw Materials for Coatings

VOC (volatile organic compound) content of raw materials for coatings is determined by measuring non-volatile material (NVM) content and water content, then calculating the balance as VOC. These measurements are done according to the procedures specified by US EPA Test Method 24, which is the method used to determine VOC content of coating formulations in the US.

NVM is determined following the test procedure described in ASTM D 2369 (Standard Test Method for Volatile Content of Coatings). Aluminum weighing pans, 58 mm in diameter, are pre-dried in a forced-draft oven at 110° C. for at least 30 minutes, then stored in a desiccator until use. The pan weights are recorded. (All weights are measured to 0.0001 g). Sample is dispensed into duplicate pans (0.3±0.1 g for samples >60 weight % NVM, 0.5±0.1 g for samples<60% NVM), with exact sample weights recorded. Into each pan, 3±1 mL purified water is dispensed and mixed with the sample and spread to cover the bottom of the pan. The pans are dried in the forced-draft oven for one hour at 110±5° C., then reweighed. Non-volatile content is calculated by difference and reported as weight percent. The VOC of Compound 1 was 7.6% (e.g the amount of material that was not volatile amounted to 85% of total material initially used) This is in contrast to the VOC content of AMP which is 100%.

Titration for pKa Values

Aqueous titrations are done on automatic titrator with 0.1; N HCl titrant, with a potentiometric probe. The titrator determines pKa from the pH vs. titrant volume curve. The pKa is equal to the pH at the titrant volume halfway to the first neutralization endpoint, corresponding to glut-bis-AMP. Endpoints are the inflection points on the curve. The pKa value recorded for the Bis-AMP analogue was 9.85. The pKa of AMP is 9.72 therefore one would expect the neutralizing capacity of Compound 1 to be similar.

Compound 3 and AMP were incorporated into a typical coating formulation as described below.

| g/5 g formulation | |
|---|---|
| 0.467 | Water |
| 0.041 | POLYPHOBE TR-116 |
| 0.068 | POLYPHOBE TR-117 |
| 0.138 | Water |
| 0.420 | Amine Neat or 10% stock solution* |
| 0.018 | TAMOL 1124 |
| 0.007 | STRODEX PK-95G |
| 0.009 | TRITON CF-10 |
| 0.024 | RHODOLINE 643 |
| 0.036 | Propylene Glycol |
| 1.408 | TIPURE R-706 |
| 0.210 | POLYGLOSS 90 |
| 2.846 | |
| 0.140 | Water |
| 2.888 | UCAR Latex 300 |
| 0.029 | TEXANOL |
| 0.012 | RHODOLINE 643 |
| 0.470 | Water |
| 6.385 | TOTAL |

*If the amine was viscous or solid, a 10% solution of the amine in water was added; the amount of amine was the same as in cases where the amine was used neat.
1. POLYPHOBE TR-116: high efficiency rheology modifier
2. POLYPHOBE TR-117: rheology modifier
3. TAMOL 1124: a dispersant
4. STRODEX PK-95G: Acid anhydride surfactant used as a dispersing/wetting agent for emulsion
5. TRITON CF-10: a non ionic surfactant
6. RHODOLINE 643: oil based defoamer
7. TIPURE R-706: titanium dioxide pigment
8. POLYGLOSS 90: an ultra-fine particle size, high brightness kaolin, designed to provide ease of dispersion and improved gloss in both aqueous and solvent-borne coatings.
9. UCAR Latex 300: vinyl acrylic polymer The formulation pH was 9.8 with compound 3 and 9.4 with AMP.

The formulations were tested for gloss and opacity. Gloss at 60° was measured with a BYK-Gardner micro-TRI-gloss meter in accordance with ASTM D 523. Opacity was measured by applying films of 3-mil wet-film thickness to opacity charts. The results were as follows:

| | AMP | compound 3 |
|---|---|---|
| opacity (equal weight) | 97.4 | 97.6 |
| opacity (equimolar) | 98 | 96 |
| gloss (equal weight) | 74.4 | 64.1 |
| gloss (equimolar) | 70.4 | 74.1 |

The invention claimed is:

1. A method for preparing a compound having formula (II)

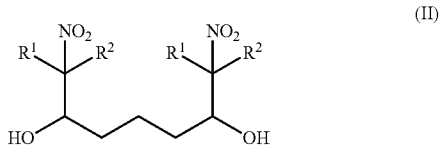

wherein $R^1$ and $R^2$ independently are methyl or ethyl, or $R^1$ and $R^2$ combine to form a $C_5$ or $C_6$ cycloalkyl or cycloalkenyl group; said method comprising combining $R^1R^2CHNO_2$, glutaraldehyde and a $C_6$-$C_{12}$ trialkylamine.

2. The method of claim 1 in which $R^1$ is methyl, $R^2$ is methyl or ethyl, or $R^1$ and $R^2$ combine to form a cyclohexyl group.

3. The method of claim 2 in which $R^1$ is methyl and $R^2$ is methyl or ethyl.

4. The method of claim 2 further comprising contacting the compound of formula (II) with a reducing agent capable of reducing aliphatic nitro groups to produce a compound of formula (I)

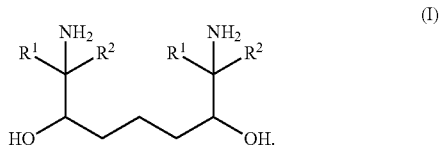

5. The method of claim 4 in which $R^1$ is methyl and $R^2$ is methyl or ethyl.

6. A method for adjusting pH in a coating composition; said method comprising adding to an aqueous coating composition having a pH below 7 a sufficient amount of a compound of formula (I) to produce a final pH from 7.5 to 9.5

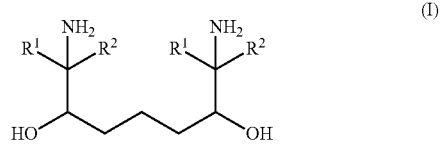

wherein $R^1$ and $R^2$ independently are methyl or ethyl, or $R^1$ and $R^2$ combine to form a $C_5$ or $C_6$ cycloalkyl or cycloalkenyl group.

7. The method of claim 6 in which $R^1$ is methyl, $R^2$ is methyl or ethyl, or $R^1$ and $R^2$ combine to form a cyclohexyl group.

8. The method of claim 7 in which the aqueous coating composition is an acrylic latex comprising polymerized units of acrylic acid, methacrylic acid, or a combination thereof.

9. The method of claim 8 in which $R^1$ is methyl and $R^2$ is methyl or ethyl.

* * * * *